United States Patent
Wilkinson et al.

(10) Patent No.: US 11,717,201 B2
(45) Date of Patent: Aug. 8, 2023

(54) FLUID COLLECTION SET PACKAGE THAT FORMS A TUBE HOLDER

(71) Applicant: Becton, Dickinson and Company, Franklin Lakes, NJ (US)

(72) Inventors: Bradley M. Wilkinson, North Haledon, NJ (US); Matthew Lee Kolb, Denville, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 265 days.

(21) Appl. No.: 17/050,631

(22) PCT Filed: Apr. 29, 2019

(86) PCT No.: PCT/US2019/029605
§ 371 (c)(1),
(2) Date: Oct. 26, 2020

(87) PCT Pub. No.: WO2019/212947
PCT Pub. Date: Nov. 7, 2019

(65) Prior Publication Data
US 2021/0228122 A1   Jul. 29, 2021

Related U.S. Application Data

(60) Provisional application No. 62/664,506, filed on Apr. 30, 2018.

(51) Int. Cl.
*A61B 5/15* (2006.01)

(52) U.S. Cl.
CPC .... *A61B 5/150305* (2013.01); *A61B 5/15003* (2013.01); *A61B 5/150732* (2013.01)

(58) Field of Classification Search
CPC .......... A61B 5/150305; A61B 5/15003; A61B 5/150732
See application file for complete search history.

(56) References Cited

U.S. PATENT DOCUMENTS

| | | | |
|---|---|---|---|
| 6,261,268 B1 | 7/2001 | Mayer | |
| 6,936,036 B2 | 8/2005 | Wilkinson et al. | |
| 2013/0178759 A1* | 7/2013 | Karpiloff | A61B 5/1438 600/576 |
| 2016/0244234 A1 | 8/2016 | Mayer et al. | |

FOREIGN PATENT DOCUMENTS

| | | |
|---|---|---|
| CN | 1556717 A | 12/2004 |
| CN | 102712407 A | 10/2012 |
| CN | 106456941 A | 2/2017 |
| EP | 1665986 B1 | 6/2009 |
| JP | 2017515555 A | 6/2017 |
| RU | 1806762 A1 | 4/1993 |
| RU | 2223794 C1 | 2/2004 |
| WO | 2006116230 A2 | 11/2006 |

* cited by examiner

*Primary Examiner* — Nathan J Jenness
*Assistant Examiner* — Severo Antonio P Lopez
(74) *Attorney, Agent, or Firm* — The Webb Law Firm

(57) ABSTRACT

A package for a needle assembly includes a tray defining a compartment in a first configuration for receiving the needle assembly. The tray can be reconfigured in a second configuration to form a holder configured to hold the needle assembly during fluid collection.

14 Claims, 9 Drawing Sheets

FLUID COLLECTION SET PACKAGE THAT FORMS A TUBE HOLDER

CROSS-REFERENCE TO RELATED APPLICATIONS

This application is the United Stated national phase of International Application No. PCT/US2019/029605 filed Apr. 29, 2019, and claims priority to United States Provisional Application Serial No. 62/664,506, entitled "Fluid Collection Set Package That Forms a Tube Holder", and filed Apr. 30, 2018, the entire disclosures of which are hereby incorporated by reference in their entirety.

BACKGROUND OF THE INVENTION

Field of the Invention

This invention relates generally to a fluid collection set and, more particularly, to a blood collection set and package wherein the package forms a holder for holding the blood collection set during blood collection.

Description of Related Art

A typical needle assembly includes a needle cannula having a proximal end, a pointed distal end and a lumen extending between the ends. A thermoplastic hub is mounted securely to the needle cannula at a location spaced from the distal end. The hub is provided with external threads or other surface configurations for removably mounting the needle cannula on another structure. Some needle assemblies are used for drawing a sample of blood or other body fluid from a patient. The needle cannulas for these assemblies typically have pointed proximal and distal ends, and the needle hub is mounted to a location between the opposed ends of the needle cannula. In other needle assemblies, a flexible tubing is mounted to the end of the hub opposite the needle cannula and in blood connection with the needle cannula, and a fitting or additional needle cannula is mounted to the end of the flexible tubing remote from the needle hub.

A needle assembly that is used to draw a sample of blood or other bodily fluid typically is used with a needle holder. The needle holder has a substantially tubular sidewall with a widely opened proximal end and a partly closed distal end. The hub of the prior art needle assembly can be engaged releasably with the partly closed distal end of the needle holder. Thus, the pointed proximal end of the needle cannula projects into the needle holder, while the pointed distal end of the needle cannula (or flexible tubing) projects distally beyond the needle holder.

The combination of a needle assembly and a needle holder is used with an evacuated tube for drawing a sample of blood or other bodily fluid from a patient. The tube has a closed end, an open end, and a sidewall extending between the ends. The tube is evacuated, and the open end is sealed by a septum that retains the vacuum within the tube. The evacuated tube is dimensioned to be slid into the open proximal end of the needle holder. Sufficient sliding of the evacuated tube into the needle holder causes the proximal point of the needle cannula to pierce the septum of the evacuated tube. Thus, the needle cannula can be placed in communication with the interior of the evacuated tube.

The needle assembly and holder are typically packaged in a sterile blister pack. The medical practitioner then removes the holder and needle assembly, inserts the first end or patient end of the needle cannula into a patient, and then inserts a fluid collection tube, such as a vacuum tube, into the holder and into contact with the second or non-patient end of the needle cannula to collect the fluid sample. Safe fluid collection practices include use of a needle shield to cover the needle after use and to allow for proper and sanitary disposal thereof. This shield can be associated with the needle holder or can be a separate member.

Manufacturing costs and packaging of these various members of the fluid collection set can be costly, so that use of the fluid collection set in economically disadvantaged communities is not possible. Oftentimes, the components are separately manufactured and assembled to form the fluid collection set. After assembly, a package is thermoformed about the contours of the holder, needle assembly, and/or the shield to form a sterile blister pack. As a cost-saving measure, these economically disadvantaged communities may attempt to reuse the holder, which could post a health risk to the medical practitioner and/or patient. Also, cross-contamination of a fluid sample could occur due to the reuse of the holder.

Accordingly, there is a need in the art that eliminates the need for the manufacturing of these multiple components of the blood collection set and that eliminates the assembly time associated therewith prior to packaging. There is also a need in the art which would prevent reuse of the needle holder.

SUMMARY OF THE INVENTION

The present invention is directed to a low-cost fluid collection set and package assembly that enables reconfiguration of the package as a holder for the fluid collection set and eliminates a need for assembly of the holder before packaging.

According to one preferred and non-limiting embodiment or aspect, provided is a package for a needle assembly comprising a tray defining a compartment in a first configuration for receiving the needle assembly, wherein the tray is configured to be reconfigured in a second configuration to form a holder configured to hold the needle assembly during fluid collection.

In one preferred and non-limiting embodiment or aspect, the tray comprises a first portion and a second portion, and wherein, in the first configuration, the first portion is connected to the second portion at a perforated connection.

In one preferred and non-limiting embodiment or aspect, in the second configuration, the first portion remains connected to the second portion at an elastic connection after the perforated connection is broken.

In one preferred and non-limiting embodiment or aspect, the first portion includes a first sidewall extending from a first peripheral flange and between a first end and a second end of the first portion, and wherein the second portion includes a second sidewall extending from a second peripheral flange and between a first end and a second end of the second portion.

In one preferred and non-limiting embodiment or aspect, in the first configuration, the first end of the first portion is at least partially removably connected to the first end of the second portion.

In one preferred and non-limiting embodiment or aspect, at least one of the second end of the first portion and the second end of the second portion comprises a removable end wall.

In one preferred and non-limiting embodiment or aspect, at least one of the first end of the first portion and the first end of the second portion comprises a removable end wall.

In one preferred and non-limiting embodiment or aspect, at least one of the second end of the first portion and the second end of the second portion comprises a removable tip.

In one preferred and non-limiting embodiment or aspect, the first peripheral flange of the first portion is configured to be connected to the second peripheral flange of the second portion.

In one preferred and non-limiting embodiment or aspect, in the second configuration, the first peripheral flange of the first portion is connected to the second peripheral flange of the second portion at a snap-fit connection or an adhesive connection.

In one preferred and non-limiting embodiment or aspect, in the second configuration, the first end of the first portion and the first end of the second portion define a distal opening in the holder, wherein the holder is configured to hold the needle assembly in the distal opening between the first end of the first portion and the first end of the second portion.

In one preferred and non-limiting embodiment or aspect, in the second configuration, the second end of the first portion and the second end of the second portion define a proximal opening in the holder for receiving a fluid collection container.

In one preferred and non-limiting embodiment or aspect, the needle assembly comprises a hub configured to support a needle cannula, and wherein, in the second configuration, the holder is configured to hold the hub in the distal opening between the first end of the first portion and the first end of the second portion such that a portion of the needle cannula is within an interior of the holder.

In one preferred and non-limiting embodiment or aspect, the holder comprises one of (i) a combination of external rings and keyways configured to the secure the needle assembly axially and circumferentially and (ii) an internal array of threads that are engagable by external threads on the needle assembly.

In one preferred and non-limiting embodiment or aspect, the tray comprises a first portion and a second portion, and wherein the first portion is connected to the second portion, and wherein the first portion is configured to fold over onto the second portion to form the holder configured to hold the needle assembly during fluid collection.

In one preferred and non-limiting embodiment or aspect, the package further comprises a removable cover configured to cover the compartment in the first configuration.

According to one preferred and non-limiting embodiment or aspect, provided is a fluid collection set comprising a needle assembly; and a package defining a compartment that receives the needle assembly in a first configuration, wherein the package is configured to be reconfigured in a second configuration to form a holder that holds the needle assembly during fluid collection.

In one preferred and non-limiting embodiment or aspect, the package comprises a first portion and a second portion, and wherein, in the first configuration, the first portion is connected to the second portion at a perforated connection.

In one preferred and non-limiting embodiment or aspect, in the second configuration, the first portion remains connected to the second portion at an elastic connection after the perforated connection is broken.

In one preferred and non-limiting embodiment or aspect, the first portion includes a first sidewall extending from a first peripheral flange and between a first end and a second end of the first portion, and wherein the second portion includes a second sidewall extending from a second peripheral flange and between a first end and a second end of the second portion.

In one preferred and non-limiting embodiment or aspect, in the first configuration, the first end of the first portion is at least partially removably connected to the first end of the second portion.

In one preferred and non-limiting embodiment or aspect, at least one of the second end of the first portion and the second end of the second portion comprises a removable end wall.

In one preferred and non-limiting embodiment or aspect, at least one of the first end of the first portion and the first end of the second portion comprises a removable end wall.

In one preferred and non-limiting embodiment or aspect, at least one of the second end of the first portion and the second end of the second portion comprises a removable tip.

In one preferred and non-limiting embodiment or aspect, the first peripheral flange of the first portion is configured to be connected to the second peripheral flange of the second portion.

In one preferred and non-limiting embodiment or aspect, in the second configuration, the first peripheral flange of the first portion is connected to the second peripheral flange of the second portion at a snap-fit connection or an adhesive connection.

In one preferred and non-limiting embodiment or aspect, in the second configuration, the first end of the first portion and the first end of the second portion define a distal opening in the holder, wherein the holder holds the needle assembly in the distal opening between the first end of the first portion and the first end of the second portion.

In one preferred and non-limiting embodiment or aspect, in the second configuration, the second end of the first portion and the second end of the second portion define a proximal opening in the holder for receiving a fluid collection container.

In one preferred and non-limiting embodiment or aspect, the needle assembly comprises a hub supporting a needle cannula, and wherein, in the second configuration, the holder holds the hub in the distal opening between the first end of the first portion and the first end of the second portion such that a portion of the needle cannula is within an interior of the holder.

In one preferred and non-limiting embodiment or aspect, the holder comprises one of (i) a combination of external rings and keyways that secure the needle assembly axially and circumferentially in the second configuration and (ii) an internal array of threads that are engaged by external threads on the needle assembly in the second configuration.

In one preferred and non-limiting embodiment or aspect, the package comprises a first portion and a second portion, and wherein the first portion is connected to the second portion, and wherein the first portion folds over onto the second portion to form the holder that holds the needle assembly during fluid collection.

In one preferred and non-limiting embodiment or aspect, the fluid collection set further comprises a removable cover that covers the compartment in the first configuration with the needle assembly within the compartment.

Other preferred and non-limiting embodiment or aspects of the present invention will be set forth in the following numbered clauses:

Clause 1. A package for a needle assembly comprising a tray defining a compartment in a first configuration for receiving the needle assembly, wherein the tray is configured to be reconfigured in a second configuration to form a holder configured to hold the needle assembly during fluid collection.

Clause 2. The package of clause 1, wherein the tray comprises a first portion and a second portion, and wherein, in the first configuration, the first portion is connected to the second portion at a perforated connection.

Clause 3. The package of clause 1 or 2, wherein, in the second configuration, the first portion remains connected to the second portion at an elastic connection after the perforated connection is broken.

Clause 4. The package of any of clauses 1-3, Wherein the first portion includes a first sidewall extending from a first peripheral flange and between a first end and a second end of the first portion, and wherein the second portion includes a second sidewall extending from a second peripheral flange and between a first end and a second end of the second portion.

Clause 5. The package of any of clauses 1-4, wherein, in the first configuration, the first end of the first portion is at least partially removably connected to the first end of the second portion.

Clause 6. The package of any of clauses 1-5, wherein at least one of the second end of the first portion and the second end of the second portion comprises a removable end wall.

Clause 7. The package of any of clauses 1-6, wherein at least one of the first end of the first portion and the first end of the second portion comprises a removable end wall.

Clause 8. The package of any of clauses 1-7, wherein at least one of the second end of the first portion and the second end of the second portion comprises a removable tip.

Clause 9. The package of any of clauses 1-8, wherein the first peripheral flange of the first portion is configured to be connected to the second peripheral flange of the second portion.

Clause 10. The package of any of clauses 1-9, wherein, in the second configuration, the first peripheral flange of the first portion is connected to the second peripheral flange of the second portion at a snap-fit connection or an adhesive connection.

Clause 11. The package of any of clauses 1-10, wherein, in the second configuration, the first end of the first portion and the first end of the second portion define a distal opening in the holder, wherein the holder is configured to hold the needle assembly in the distal opening between the first end of the first portion and the first end of the second portion.

Clause 12. The package of any of clauses 1-11, wherein, in the second configuration, the second end of the first portion and the second end of the second portion define a proximal opening in the holder for receiving a fluid collection container.

Clause 13. The package of any of clauses 1-12, wherein the needle assembly comprises a hub configured to support a needle cannula, and wherein, in the second configuration, the holder is configured to hold the hub in the distal opening between the first end of the first portion and the first end of the second portion such that a portion of the needle cannula is within an interior of the holder.

Clause 14. The package of any of clauses 1-13, wherein the holder comprises one of (i) a combination of external rings and keyways configured to the secure the needle assembly axially and circumferentially and (ii) an internal array of threads that are engagable by external threads on the needle assembly.

Clause 15. The package of any of clauses 1-14, wherein the tray comprises a first portion and a second portion, and wherein the first portion is connected to the second portion, and wherein the first portion is configured to fold over onto the second portion to form the holder configured to hold the needle assembly during fluid collection.

Clause 16. The package of any of clauses 1-15, further comprising a removable cover configured to cover the compartment in the first configuration.

Clause 17. A fluid collection set comprising a needle assembly; and a package defining a compartment that receives the needle assembly in a first configuration, wherein the package is configured to be reconfigured in a second configuration to form a holder that holds the needle assembly during fluid collection.

Clause 18. The fluid collection set of clause 17, wherein the package comprises a first portion and a second portion, and wherein, in the first configuration, the first portion is connected to the second portion at a perforated connection.

Clause 19. The fluid collection set of clause 17 or 18, wherein, in the second configuration, the first portion remains connected to the second portion at an elastic connection after the perforated connection is broken.

Clause 20. The fluid collection set of any of clauses 17-19, wherein the first portion includes a first sidewall extending from a first peripheral flange and between a first end and a second end of the first portion, and wherein the second portion includes a second sidewall extending from a second peripheral flange and between a first end and a second end of the second portion.

Clause 21. The fluid collection set of any of clauses 17-20, wherein, in the first configuration, the first end of the first portion is at least partially removably connected to the first end of the second portion.

Clause 22. The fluid collection set of any of clauses 17-21, wherein at least one of the second end of the first portion and the second end of the second portion comprises a removable end wall.

Clause 23. The fluid collection set of any of clauses 17-22, wherein at least one of the first end of the first portion and the first end of the second portion comprises a removable end wall.

Clause 24. The fluid collection set of any of clauses 17-23, wherein at least one of the second end of the first portion and the second end of the second portion comprises a removable tip.

Clause 25. The fluid collection set of any of clauses 17-24, wherein the first peripheral flange of the first portion is configured to be connected to the second peripheral flange of the second portion.

Clause 26. The fluid collection set of any of clauses 17-25, Wherein, in the second configuration, the first peripheral flange of the first portion is connected to the second peripheral flange of the second portion at a snap-fit connection or an adhesive connection.

Clause 27. The fluid collection set of any of clauses 17-26, wherein, in the second configuration, the first end of the first portion and the first end of the second portion define a distal opening in the holder, wherein the holder holds the needle assembly in the distal opening between the first end of the first portion and the first end of the second portion.

Clause 28. The fluid collection set of any of clauses 17-27, wherein, in the second configuration, the second end of the first portion and the second end of the second portion define a proximal opening in the holder for receiving a fluid collection container.

Clause 29. The fluid collection set of any of clauses 17-28, wherein the needle assembly comprises a hub supporting a needle cannula, and wherein, in the second configuration, the holder holds the hub in the distal opening between the first end of the first portion and the first end of the second portion such that a portion of the needle cannula is within an interior of the holder.

Clause 30. The fluid collection set of any of clauses 17-29, wherein the holder comprises one of (i) a combination of external rings and keyways that secure the needle assembly axially and circumferentially in the second configuration and (ii) an internal array of threads that are engaged by external threads on the needle assembly in the second configuration.

Clause 31. The fluid collection set of any of clauses 17-30, wherein the package comprises a first portion and a second portion, and wherein the first portion is connected to the second portion, and wherein the first portion folds over onto the second portion to form the holder that holds the needle assembly during fluid collection.

Clause 32. The fluid collection set of any of clauses 17-31, further comprising a removable cover that covers the compartment in the first configuration with the needle assembly within the compartment.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWING(S)

Figure 4D:
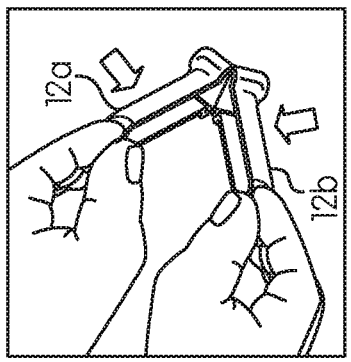
Figure 4C:
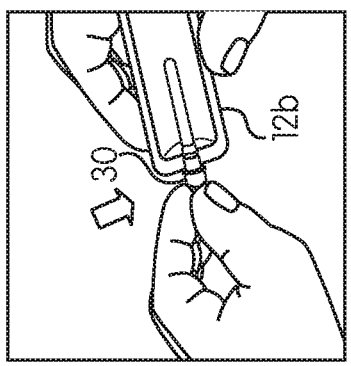
Figure 4B:
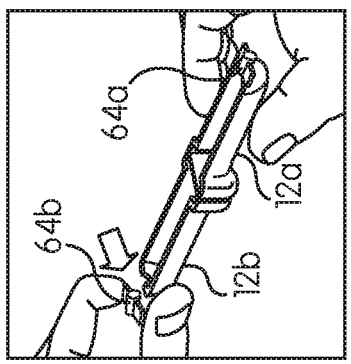
Figure 4A:
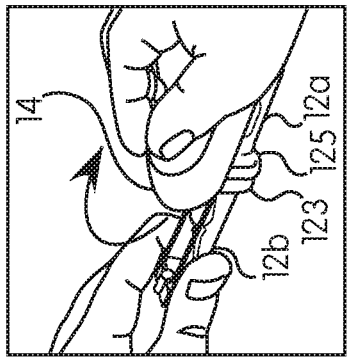
Figure 4E:
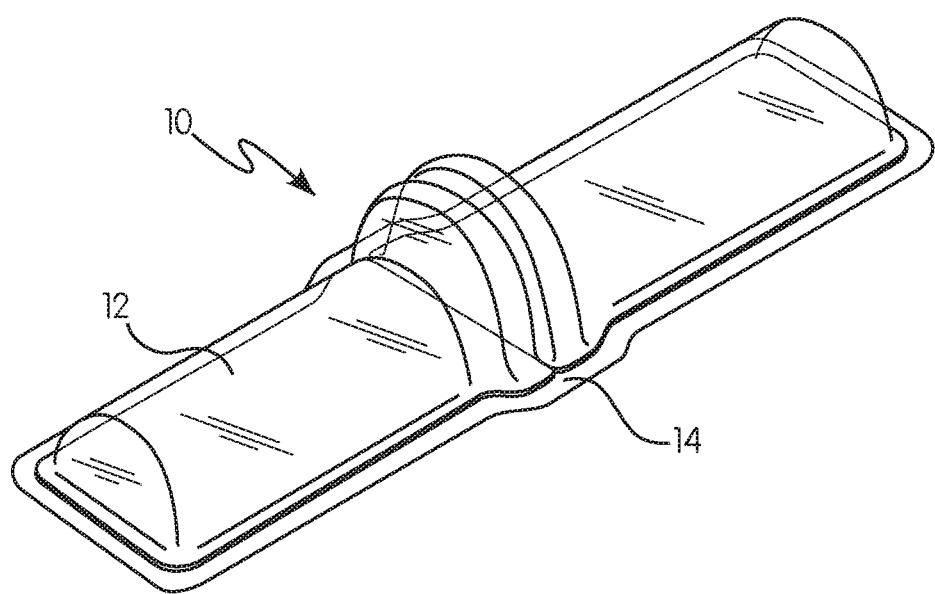
Figure 5:
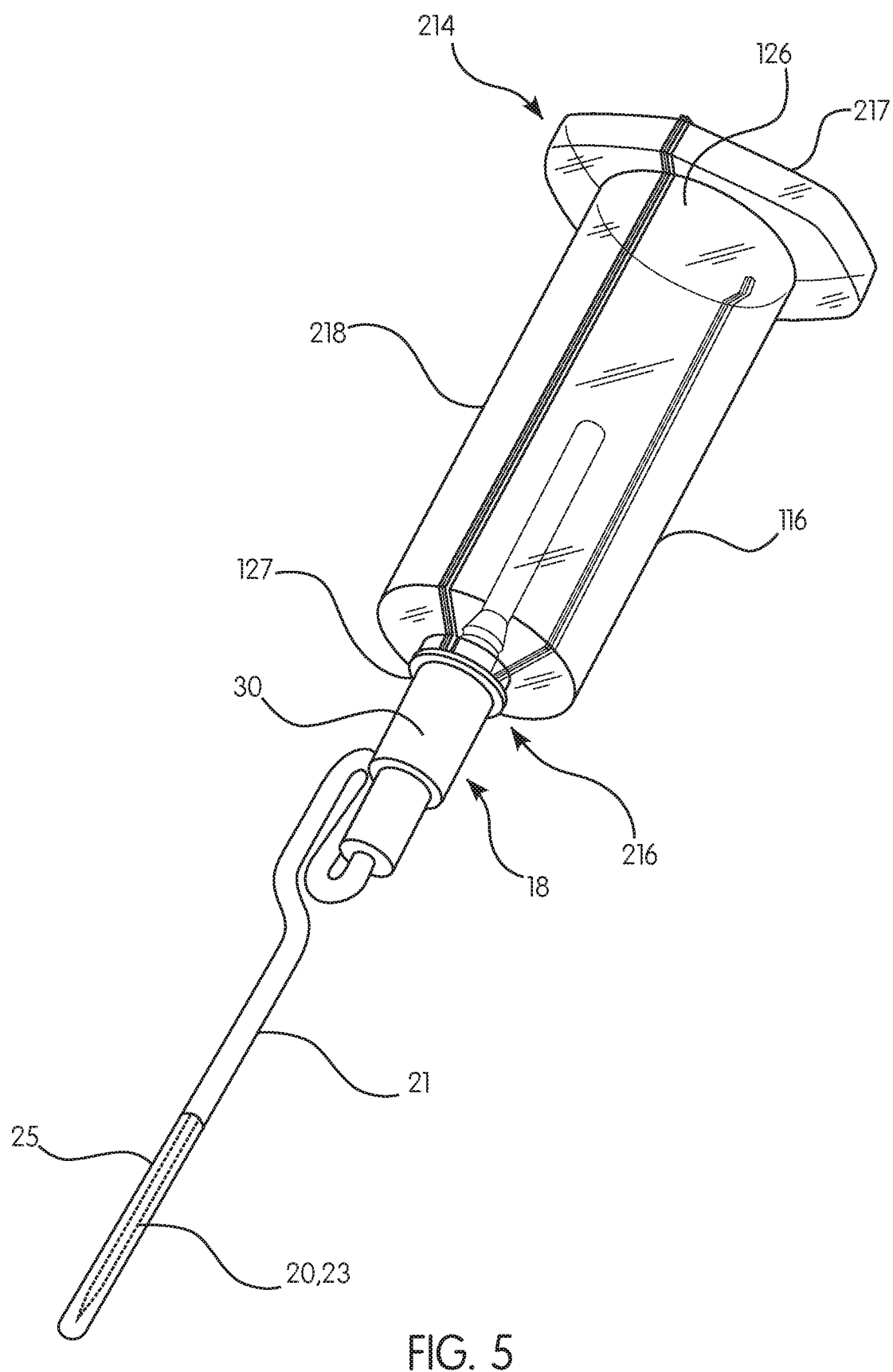

FIGS. 4A-D is a perspective view of stages for assembling a fluid collection set from a fluid collection set package according to principles of the present invention;

FIG. 4E is a perspective view of a package according to principles of the present invention; and FIG. 5 is a perspective view of an assembled fluid collection set according to principles of the present invention.

DESCRIPTION OF THE INVENTION

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It will be noted that the term "distal" as used herein refers to the end of the needle assembly that punctures the patient's skin while "proximal" means the end of the needle assembly that punctures an evacuated container.

Figure 1A:
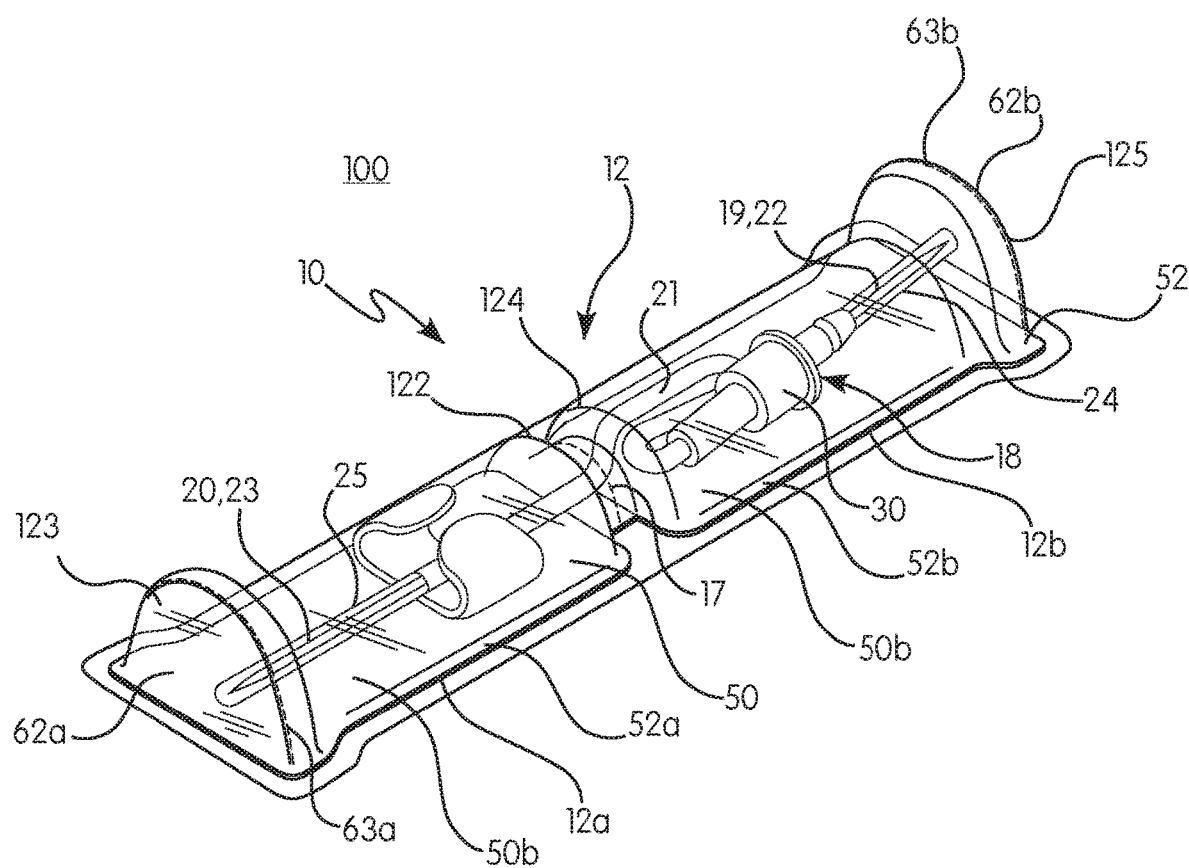
FIG. 1A is a perspective view of a fluid collection set package according to principles of the present invention.
Figure 1B:
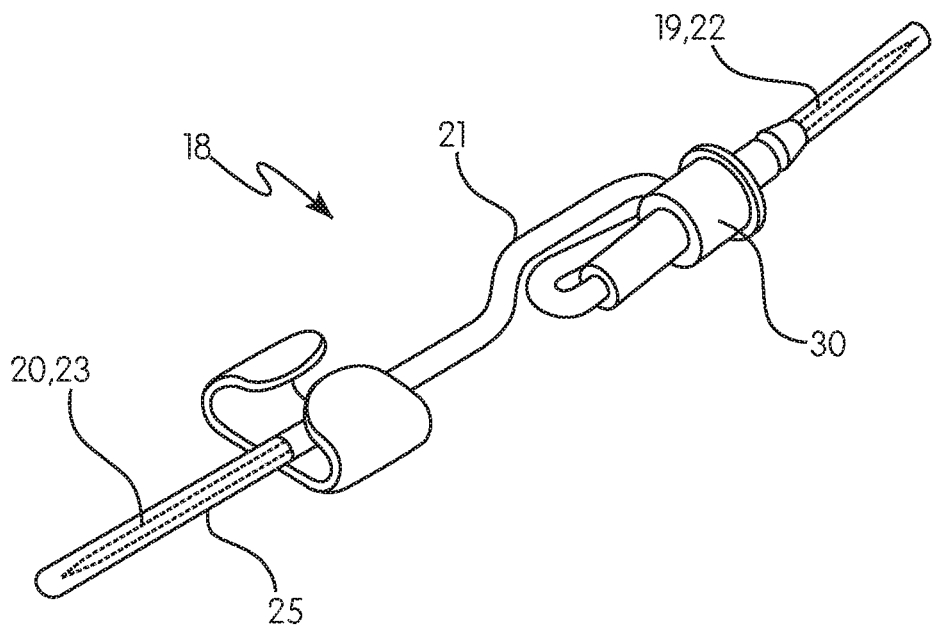
FIG. 1B is a perspective view of a needle assembly according to principles of the present invention.
Figure 1C:
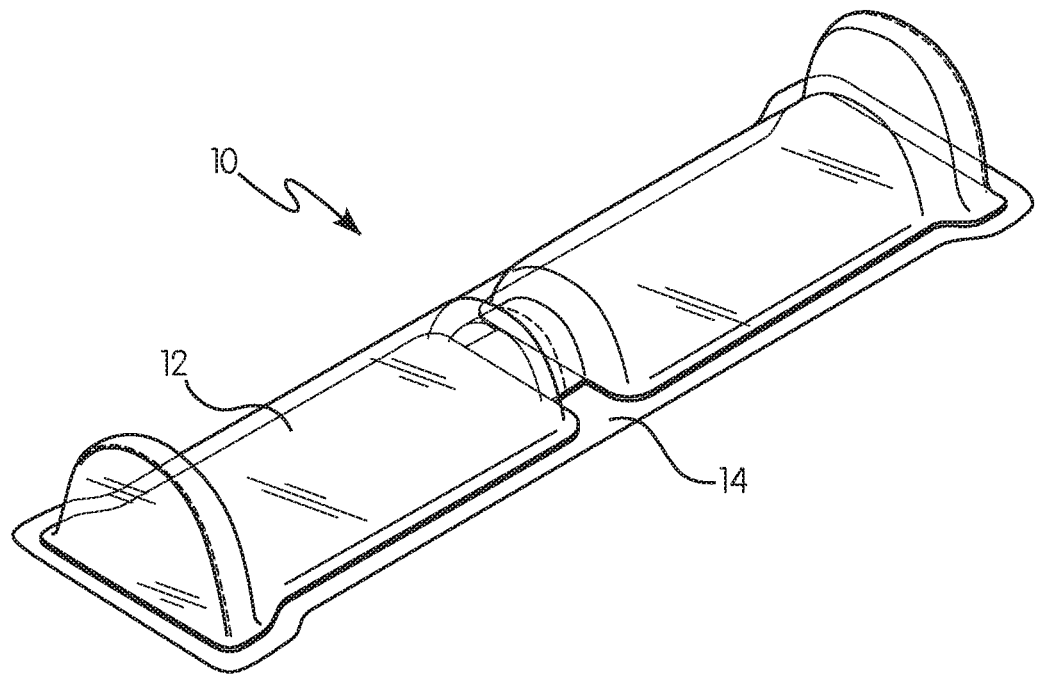
FIG. 1C is a perspective view of a package according to principles of the present invention.

Referring to FIGS. 1A-C and 2, a fluid collection set 100 according to a preferred and non-limiting embodiment or aspect includes a package 10 including a tray 12 and a removable cover 14, and a needle assembly 18. FIG. 1B shows needle assembly 18 without package 10. FIG. 1C shows package 10 including tray 12 and cover 14 without needle assembly 18. The tray 12 defines a compartment 60 for receiving the needle assembly 18, which can be covered by the removable cover 14, as described in more detail below.

Figure 3A:
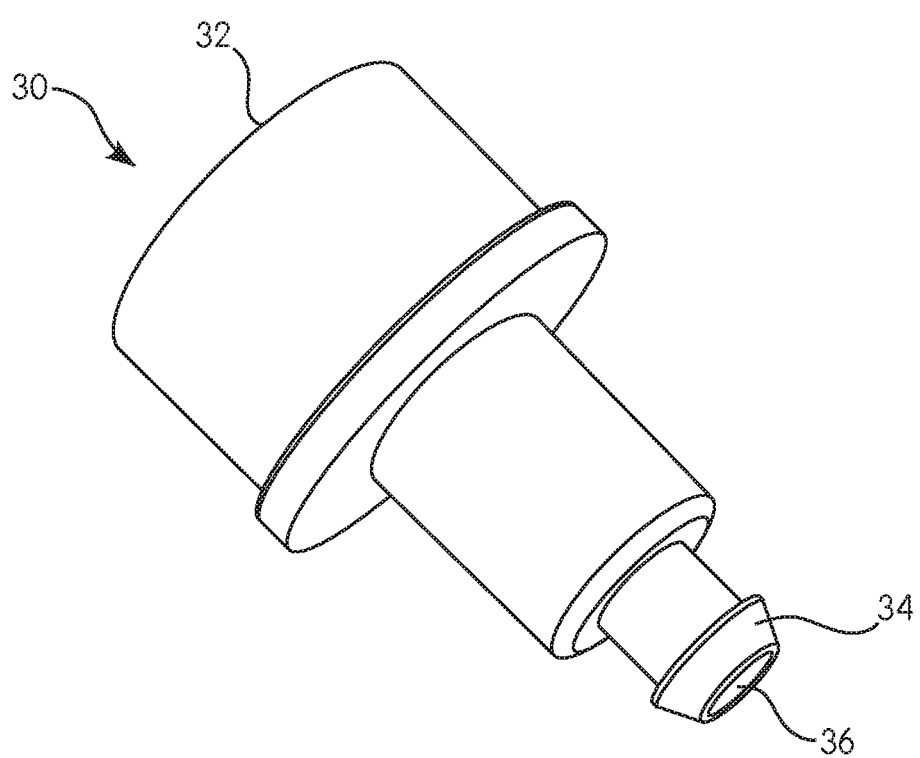
FIG. 3A is a perspective view of a hub for a needle assembly according to principles of the present invention.
Figure 3B:
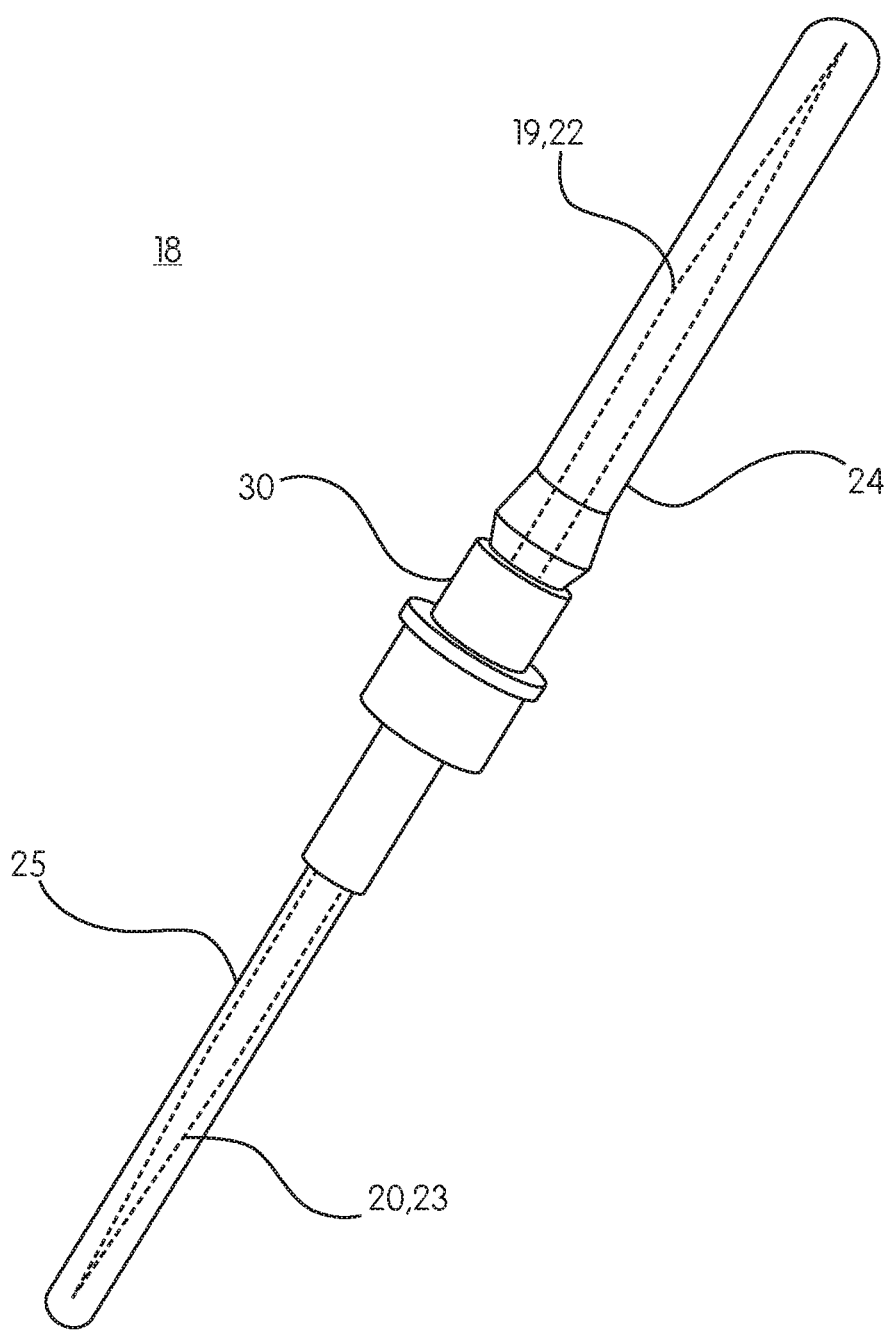
FIG. 3B is a perspective view of a double-ended needle assembly according to principles of the present invention.

Referring also to FIGS. 3A and 3B, the needle assembly 18 includes a needle cannula 19 and a hub 30, which is configured for supporting the needle cannula 19. It can be appreciated that the needle assembly 18 and hub 30 can be of any known design and that the hub 30 shown in FIG. 3A is only one type of hub that can be used for supporting the needle cannula 19. The hub 30 includes a distal or patient end 32, a proximal or non-patient end 34, and a passage 36 extending between the distal and proximal ends 32, 34. In a double-ended needle implementation, as shown in FIG. 3B, the needle cannula 19 is associated with the hub 30 such that a lumen of the needle cannula 19 is located within and extends through the passage 36 of the hub 30 and a first or patient end 20 extends through the distal or patient end 32 of the hub and a second or non-patient end 22 extends through the proximal or non-patient end 34 of the hub 30. In a single-ended needle implementation as shown in FIG. 1A, the needle cannula 19 is associated with the hub 30 such that a lumen of the needle cannula 19 is in fluid connection with one end of a length of flexible tubing 21 connected to the hub 30 at the distal or patient end 32, and the second or non-patient end 22 of the needle cannula 19 extends from the proximal or non-patient end 34 of the hub 30. The other end of the flexible tubing 21 can be in fluid connection with a patient cannula 23. A sheath or pierceable cover 24 can be located about the second or non-patient end 22 of needle cannula 19 of the needle assembly. A removable shield 25 can be located about the patient cannula 23 or the first or patient end 20.

Figure 2:
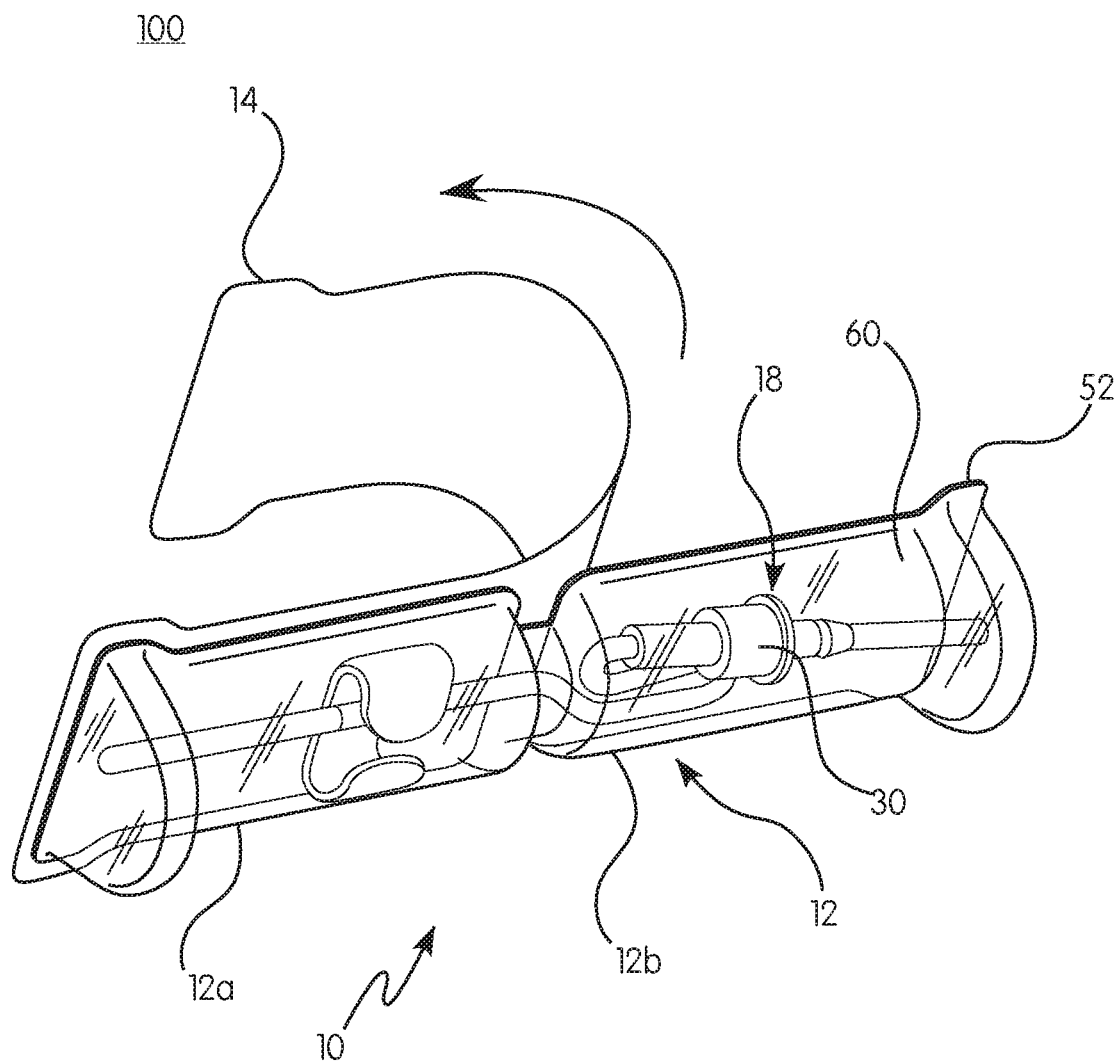
FIG. 2 is a perspective view of a fluid collection set package according to principles of the present invention.
Figure 3C:
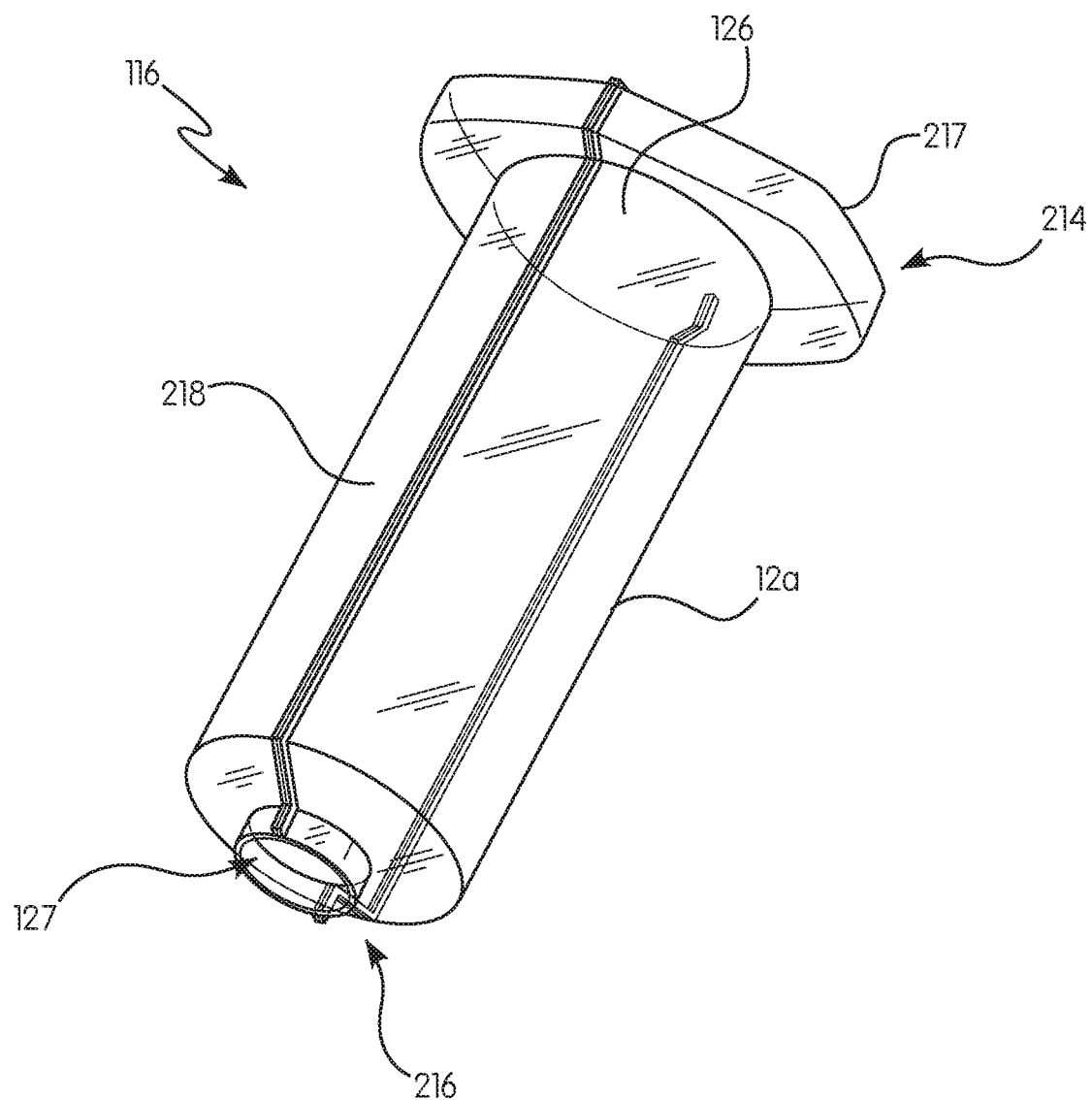
FIG. 3C is a perspective view of a holder according to principles of the present invention.

The tray 12 may be a blister package and can be molded unitarily from a thermoplastic material. The tray 12 includes a sidewall 50 extending from a peripheral flange 52 to define the compartment 60 for receiving the needle assembly 18 in the first configuration of the tray 12, as shown in FIGS. 1 and 2. The tray 12 is configured to be reconfigured in a second configuration to form a holder 116 configured to hold the needle assembly 18 during fluid collection, as shown in FIGS. 3C and 5. The tray 12 as described herein may be shaped to form holder 116 as shown in FIGS. 3C and 5 or shaped to form other holders known in the art. The tray 12 comprises a first portion 12a connected to a second portion 12b in the first configuration. The first portion 12a and the second portion 12b define the compartment 60 for receiving the needle assembly 18 in the first configuration. The first portion 12a may be at least partially removably connected to the second portion 12b. For example, the first portion 12a and the second portion 12b can be connected at a perforated connection 17 of the tray 12, In some embodiments, the perforated connection 17 enables the first portion 12a to be completely separated from the second portion 12b. In other embodiments, the perforated connection 17 enables only a portion of the first portion 12a to be separated from a portion of the second portion 12b, i.e., at the area of the perforated connection 17, with the first portion 12a and the second portion 12b remaining connected at the peripheral flange 52 such that the first portion 12a can fold over onto the second portion 12b to form the holder 116 configured to hold the needle assembly 18 during fluid collection after the perforated connection 17 is broken. For example, the peripheral flange 52 can provide an elastic connection between the first portion 12a and the second portion 12b.

The first portion 12a of the tray 12 includes a first sidewall 50a extending from a first peripheral flange 52a and between a first end 122 and a second end 123 of the first portion 12a. The second portion 12b includes a second sidewall 50b extending from a second peripheral flange 52b and between a first end 124 and a second end 125 of the second portion 12b. In one embodiment, as shown in FIG. 1A, in the first configuration, the first end 122 of the first portion 12a is connected to the first end 124 of the second portion 12b at the perforated connection 17 and/or at the peripheral flange 52. The second end 123 of the first portion 12a and the second end 125 of the second portion 12b respectively comprise removable end walls 62a, 62b. For example, the removable end wall 62a may form a sidewall enclosing the second end 123 of the first portion 12a that can be removed by breaking a perforated connection 63a between the removable end wall 62a and the remainder of the first sidewall 50a, and the removable end wall 62b may form a sidewall enclosing the second end 125 of the second portion 12b that can be removed by breaking a perforated connection 63b between the removable end wall 62b and the remainder of the second sidewall 50b.

In another embodiment, as shown in FIGS. 4A-E, in the first configuration, the second end 123 of the first portion 12a can be connected at the peripheral flange 52 to the second end 125 of the second portion 12b at an elastic connection. For example, the first portion 12a may be configured to fold over onto the second portion 12b to form the holder 116 configured to hold the needle assembly 18 during fluid collection. The first portion 12a may remain elastically connected to the second portion 12b in the second configuration at the peripheral flange 52, and the second end 123 of the first portion 12a and the second end 125 of the second portion 12b can respectively comprise the removable end walls 62a, 62b which can be removed to form proximal opening 126 as discussed in more detail herein. The first end 122 of the first portion 12a and the first end of the second portion 12b may respectively comprise removable tips 64a, 64b that can be removed by breaking a perforated or scored connection between the removable tips 64a, 64b and the first end 122, 124 of the first and second portion 12a, 12b. In another implementation, e second end 123 of the first portion 12a can be connected at the peripheral flange 52 to the second end 125 of the second portion 12b with the perforated connection 17 such that the first portion 12a and can be partially or completely separated from the second portion 12b.

The removable cover 14 can be applied to the peripheral flange 52 with the needle assembly 18 received within the compartment 60. The compartment 60 can be sized and shaped such that the needle assembly 18 can be received within the compartment 60 without any portion of the needle assembly extending beyond a plane defined by the peripheral flange 52 of the tray 12. The removable cover 14 can be adhered or bonded removably to the peripheral flange 52 with the needle assembly 18 within the compartment 60. The needle assembly 18 can be accessed by peeling removable cover 14 from peripheral flange 52 substantially in a conventional manner for blister packages.

The first peripheral flange 52a of the first portion 12a is configured to be connected to the second peripheral flange 52b of the second portion 12b. For example, as shown in FIG. 4A, a user can peel off the removable cover 14 from the tray 12. As shown in FIG. 4B, the user removes the needle assembly 18 from the tray 12 and breaks off the removable tips 64a, 64b, As shown in FIG. 4C, the user places the hub 30 of the needle assembly 18 into the area where one of the removable tips 64a or 64b was removed, i.e., at one of the first end 122 of the first portion 12a and the first end 124 of the second portion 12b. As shown in FIG. 4D, the user folds one of the first portion 12a and the second portion 12b onto the other of the first portion 12a and the second portion 12b to form the holder 116 as shown in FIGS. 3C and 5. In the second configuration of the tray 12, the first peripheral flange 52a of the first portion 12a can be connected to the second peripheral flange 52b of the second portion 12b by a snap-fit connection or an adhesive connection. In another embodiment, a band or wrap may be placed around the exterior of the first portion 12a and the second portion 12b to hold the first portion 12a, and the second portion 12b together in the second configuration. The removable end walls 62a, 62b can be broken off from the remainder of the tray 12 at any time during the process of forming the holder 116.

Alternatively, in an embodiment as shown in FIG. 1A, the user can break the perforated connection 17 and place the first portion 12a onto the second portion 12b (or fold the first portion 12a onto the second portion 12b if an elastic connection at the peripheral flange 52 is present) with the first end 122 of the first portion 12a aligned with the first end 124 of the second portion 12b to form the holder 116 as shown in FIGS. 3C and 5.

Referring to FIGS. 3C and 5, the holder 116 has a proximal end 214, a distal end 216 and a tubular sidewall 218 extending between ends 214 and 216. In the second configuration, the second end 123 of the first portion 12a and the second end 125 of the second portion 12b define a proximal opening 126 in the holder 116 for receiving a fluid collection container. For example, by removing the removable end walls 62a, 62b, the proximal opening 126 to the interior of the holder 116 can be created when the tray 12 is in the second configuration. The proximal end 214 of the holder 116 may have a radially aligned finger flange 217 to facilitate manipulation of holder 116. Finger flange 217 may be non-circular to prevent holder 116 from rolling. Finger flange 217 preferably has a linear edge to provide a clear indication of the top and bottom sides.

In the second configuration, the first end 122 of the first portion 12a and the first end 124 of the second portion 12b are configured to define a distal opening 127 in the holder 116, wherein the holder 116 is configured to hold the needle assembly 18 in the distal opening 127 between the first end 122 of the first portion 12a and the first end 124 of the second portion 12b. For example, by breaking the perforation 17 as shown in FIGS. 1 and 2 or removing the removable tips 64a, 64b as shown in FIG. 4, the distal opening 127 in which the needle assembly 18 can be held between the first end 122 of the first portion 12a and the first end 124 of the second portion 12b can be created when the tray 12 is in the second configuration as shown in FIGS. 3C and 5. Distal end 216 of holder 116 includes structure to which needle assembly 18 is mounted. In particular, distal end 216 of needle holder 116 may be formed with non-threaded mounting means, such that needle holder 116 is substantially fixed to needle assembly 18 after assembly. The non-threaded mounting means comprises a combination of external rings and keyways to secure needle assembly 18 axially and circumferentially. Alternately, the distal end 216 of the needle holder 116 may be formed with an internal array of threads that are engagable by external threads on the needle assembly 18.

In operation, the patient cannula 23 or the first or patient end 20 of the needle assembly 18 is inserted into a collection site, such as a patient's vein, and a collection container is inserted into the holder 116 through proximal opening 126 such that the second or non-patient end 22 of the needle assembly 18 is displaced and pierces sheath 24 and subsequently pierces a resealable member and/or gas barrier member of the collection container. Once the non-patient end 22 is in fluid communication with the collection container, the vacuum within the collection container applies a force to the blood specimen to draw it into the collection container.

Although the invention has been described in detail for the purpose of illustration based on what is currently considered to be the most practical and preferred embodiments or aspects, it is to be understood that such detail is solely for that purpose and that the invention is not limited to the disclosed embodiments or aspects, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A package for a needle assembly comprising:
a tray defining a compartment in a first configuration for receiving the needle assembly, wherein the tray is configured to be reconfigured in a second configuration to form a holder configured to hold the needle assembly during fluid collection, wherein the tray comprises a first portion and a second portion, wherein the first portion includes a first sidewall extending from a first peripheral flange and between a first end and a second end of the first portion, wherein the second portion includes a second sidewall extending from a second peripheral flange and between a first end and a second end of the second portion, wherein, in the first configuration, the first end of the first portion is at least partially removably connected to the first end of the second portion, wherein, in the second configuration, the first end of the first portion and the first end of the second portion define a distal opening in the holder, and wherein the holder is configured to hold the needle assembly in the distal opening between the first end of the first portion and the first end of the second portion.

2. The package of claim 1, wherein, in the first configuration, the first end of the first portion is at least partially removably connected to the first end of the second portion at a perforated connection.

3. The package of claim 2, wherein, in the second configuration, the first portion remains connected to the second portion at an elastic connection after the perforated connection is broken.

4. The package of claim 3, wherein the first portion is configured to fold over onto the second portion to form the holder configured to hold the needle assembly during fluid collection.

5. The package of claim 2, wherein, in the second configuration, the first peripheral flange of the first portion is configured to be connected to the second peripheral flange of the second portion by a snap-fit connection or an adhesive connection.

6. The package of claim 1, wherein, in the second configuration, the second end of the first portion and the second end of the second portion define a proximal opening in the holder for receiving a fluid collection container.

7. The package of claim 1, further comprising a removable cover configured to cover the compartment in the first configuration.

8. A fluid collection set comprising:
a needle assembly; and
a package defining a compartment that receives the needle assembly in a first configuration, wherein the package is configured to be reconfigured in a second configuration to form a holder that holds the needle assembly during fluid collection, wherein the package comprises a first portion and a second portion, wherein the first portion includes a first sidewall extending from a first peripheral flange and between a first end and a second end of the first portion, wherein the second portion includes a second sidewall extending from a second peripheral flange and between a first end and a second end of the second portion, wherein, in the first configuration, the first end of the first portion is at least partially removably connected to the first end of the second portion, wherein, in the second configuration, the first end of the first portion and the first end of the second portion define a distal opening in the holder, and wherein the holder holds the needle assembly in the distal opening between the first end of the first portion and the first end of the second portion.

9. The fluid collection set of claim 8, wherein, in the first configuration, the first end of the first portion is at least partially removably connected to the first end of the second portion at a perforated connection.

10. The fluid collection set of claim 9, wherein, in the second configuration, the first portion remains connected to the second portion at an elastic connection after the perforated connection is broken.

11. The fluid collection set of claim 10, wherein the first portion folds over onto the second portion to form the holder that holds the needle assembly during fluid collection.

12. The fluid collection set of claim 8, wherein, in the second configuration, the second end of the first portion and the second end of the second portion define a proximal opening in the holder for receiving a fluid collection container.

13. The fluid collection set of claim 8, wherein the needle assembly comprises a hub supporting a needle cannula, and wherein, in the second configuration, the holder holds the hub in the distal opening between the first end of the first portion and the first end of the second portion such that a portion of the needle cannula is within an interior of the holder.

14. The fluid collection set of claim 8, further comprising a removable cover that covers the compartment in the first configuration with the needle assembly within the compartment.

* * * * *

UNITED STATES PATENT AND TRADEMARK OFFICE
CERTIFICATE OF CORRECTION

PATENT NO. : 11,717,201 B2
APPLICATION NO. : 17/050631
DATED : August 8, 2023
INVENTOR(S) : Wilkinson et al.

It is certified that error appears in the above-identified patent and that said Letters Patent is hereby corrected as shown below:

In the Specification

Column 1, Line 7, delete "Stated" and insert -- States --

Signed and Sealed this
Third Day of October, 2023

Katherine Kelly Vidal
*Director of the United States Patent and Trademark Office*